(12) United States Patent
Krumpl

(10) Patent No.: US 10,722,516 B2
(45) Date of Patent: Jul. 28, 2020

(54) USE OF LANDIOLOL HYDROCHLORIDE IN THE LONG-TERM TREATMENT OF TACHYARRHYTHMIAS

(71) Applicant: AOP Orphan Pharmaceuticals AG, Vienna (AT)

(72) Inventor: Günther Krumpl, Vienna (AT)

(73) Assignee: AOP ORPHAN PHARMACEUTICALS AG, Vienna (AT)

( * ) Notice: Subject to any disclaimer, the term of this patent is extended or adjusted under 35 U.S.C. 154(b) by 0 days.

(21) Appl. No.: 14/787,217

(22) PCT Filed: Apr. 25, 2014

(86) PCT No.: PCT/EP2014/058456
§ 371 (c)(1),
(2) Date: Oct. 26, 2015

(87) PCT Pub. No.: WO2014/174076
PCT Pub. Date: Oct. 30, 2014

(65) Prior Publication Data
US 2016/0074411 A1 Mar. 17, 2016

(30) Foreign Application Priority Data
Apr. 26, 2013 (EP) .................................. 13165582

(51) Int. Cl.
*A61K 31/5377* (2006.01)
*A61K 9/08* (2006.01)

(52) U.S. Cl.
CPC ............ *A61K 31/5377* (2013.01); *A61K 9/08* (2013.01); *Y10S 514/821* (2013.01)

(58) Field of Classification Search
None
See application file for complete search history.

(56) References Cited

U.S. PATENT DOCUMENTS

2010/0311738 A1\* 12/2010 Widmann ............ A61K 9/0019
514/231.5

FOREIGN PATENT DOCUMENTS

| CN | 1827109 | A | 9/2006 |
| CN | 101732319 | A | 6/2010 |
| CN | 102232930 | A | 11/2011 |
| CN | 102475706 | A | 5/2012 |
| JP | 2004323370 | A | 11/2004 |
| JP | 2005068107 | A | 3/2005 |
| JP | 2010248263 | A | 11/2010 |
| NZ | 586200 | A | 6/2012 |

OTHER PUBLICATIONS

Li, Study on Quality and Stability of Landiolol Hydrochloride, GlobeThesis.com, Jan. 8, 2011, printed from http://www.globethesis.com/?t=2194330332980124, 2 pages, Abstract only.\*
Landiolol, MeSH—NCBI, printed from https://www.ncbi.nlm.nih.gov/mesh/67077049 on Apr. 19, 2017, 1 page.\*
www.thepharmaletter.com, State of development in Ono Pharma R&D pipeline, Nov. 10, 1999, printed from https://www.thepharmaletter.com/article/state-of-development-in-ono-pharma-r-d-pipeline, 2 pages.\*
Reingardiene, The consequence of epinephrine (adrenaline) overdose, Medicina (Kaunas). 2006;42(7):606-9, printed from https://www.ncbi.nlm.nih.gov/pubmed/16861845, Abstract only, 1 page.\*
Daubert et al., Acute clenbuterol overdose resulting in supraventricular tachycardia and atrial fibrillation, J Med Toxicol. 2007 Jun;3(2):56-60, printed from https://www.ncbi.nlm.nih.gov/pubmed/18072161, Abstract only, 2 pages (Year: 2007).\*
Nakano et al., Effect of landiolol hydrochloride, an ultra-short-acting beta 1-selective blocker, on supraventricular tachycardia, atrial fibrillation and flutter after pulmonary resection, J Clin Pharm Ther. Aug. 2012;37(4):431-435, Epub Nov. 7, 2011(Year: 2011).\*
Morishima et al. (2009). Suppressive Effect of Landiolol Hydrochloride on Atrial Fibrillation Following Surgical Repair of Acute Type A Aortic Dissection. Jpn. J. Vasc Surg.. 18. 481-485, English Abstract.\*
Ito et al., Use of landiolol in the perioperative management of supraventricular tachycardia, J Anesth. 2006;20(3):253-4.\*
Atarashi et al., Pharmacokinetics of landiolol hydrochloride, a new ultra-short-acting beta-blocker, in patients with cardiac arrhythmias, Clin Pharmacol Ther. Aug. 2000;68(2):143-50, printed from https://www.ncbi.nlm.nih.gov/pubmed/10976545, 2 pages, abstract only.\*
Nojiri et al., Gen Thorac Cardiovasc Surg (2011) 59: 799.\*
Goto et al, "The effect of landiolol on hemodynamics and left ventricular function in patients with coronary artery disease", 2007, J Clinical Anesthesia, 19, pp. 523-529.
Koracevic, Goran "Significance of "beta blocker rebound phenomenon" and new suggestions how to avoid it", Proceedings of the World Medical Conference, 2011; ISBN: 978-1-61804-036-7; 6 pages.
"ONOACT landiolol hydrochloride for injection" data sheet; Revised May 2015; 18 pages.
Alhashemi, "Treatment of cardiogenic shock with levosimendan in combination with B-adrenergic antagonists" Brit.J.Anaesthes., 2005, 95(5), 648-650.
Anderson, "Management of Beta-Adrenergic Blocker Poisoning" 2008, Clin.Ped.Emergency Med., 4-20.
Harrison et al, "Discontinuation of Propanolol Therapy", 1976, Chest, 69(1), pp. 1-2.
Hausen, "Absetzsyndrom nach Betablocker-Therapie" 1981, MMW Münch Med Wochenschr., 123(42), 1583-1584.
Heilbrunn et al, "Increased beta-receptor density and improved hemodynamic response to catecholamine stimulation during long-term metoprolol therapy in heart failure from dilated cardiomyopathy", Circulation, 1989, 79, 483-490.

(Continued)

*Primary Examiner* — Gigi G Huang
(74) *Attorney, Agent, or Firm* — Loza & Loza, LLP; Michael F. Fedrick

(57) ABSTRACT

The invention provides a new use of landiolol hydrochloride for persistent reduction of the heart rate during the administration period of landiolol hydrochloride in the treatment of a human suffering from tachycardia, tachyarrhythmia or elevated blood pressure, wherein landiolol hydrochloride is administered at a constant dose of more than 5 µg/kg/min, specifically of at least 10 µg/kg/min for a period of at least 2 hours and wherein the heart rate and/or blood pressure of said patient are persistently reduced during the administration period compared to the heart rate and/or blood pressure before treatment and no overshooting effect occurs after termination of said administration.

15 Claims, No Drawings

(56) References Cited

OTHER PUBLICATIONS

Kubo et al, "Successful management of cesarean section in a patient with Romano-Ward syndrome using landiolol, a selective and short-acting B1 receptor antagonist", Journal of Anethesia, Springer-Verlag, TO, vol. 19, No. 2, 2005, pp. 174-176.
Miwa et al, "Effects of Landiolol, an Ultra-Short-Acting B1-Selective Blocker, on Electrical Storm Refractory to Class III Antiarrhythmic Drugs", Circulation Journal: Official Journal of the Japanese Circulation Society May 2010, vol. 74, No. 5, pp. 856-863.
Mizuno et al, "Age and sex-related differences in dose-dependent hemodynamic response to landiolol hydrochloride during general anesthesia", European Journal of Clinical Pharmacology, Springer, Berlin, DE, vol. 63, No. 3, 2007, pp. 243-252.
Morisaki et al, "Very-low-dose continuous drip infusion of landiolol hydrochloride for postoperative atrial tachyarrhythmia in patients with poor left ventricular function", General Thoracic and Cardiovascular Surgery, 2012, vol. 60, No. 6, pp. 386-390.
Murakami et al, "Pharmacokinetics and Pharmacodynamics of Landiolol Hydrochloride, an Ultra Short-acting B1-Selective Blocker, in a Dose Esclalation Regimen in Healthy Male Volunteers", Drug Metab. Pharmacokinet., 2005, 20(5), 337-344.
Nagai et al, "Urgent Management of Rapid Heart Rate in Patients With Atrial Fibrillation/Flutter and Left Ventricular Dysfunction", Circulation Journal: Official Journal of the Japanese Circulation Society 2013, vol. 77, No. 4, 2013, pp. 308-916.
Niakano et al, "Effect of landiolol hydrochloride, an ultra-short-acting beta 1-selective blocker, on supraventricular tachycardia, atrial fibrillation and flutter after pulmonary resection", Journal of Clinical Pharmacy and Therapeutics, vol. 37, No. 4, 7. Aug. 2012, pp. 431-435.
Nanoff et al, "Desensitization pattern of cardiac B-adrenoceptor subtypes by prolonged in vivo infusion of pindolol and celiprolol in rats" 1990, Basic Res. Cardiol., 85, 88-95.
Peters et al, "Enhanced adenylate cyclase activity of turkey erythrocytes following treatment with B-adrenergic receptor antagonists", 1984, 107, 43-52.
Takahashi et al, "Landiolol decreases a dysrhythmogenic dose of epinephrine in dogs during halothane anesthesia", Canadian Journal of Anaesthesia, vol. 46, No. 6, 6 Jun. 1999, pp. 599-604.
Takahashi et al, "Modifications of the hemodynamic consequences of theophylline intoxication with landiolol in halothane-anesthetized dogs", Canadian Journal of Anesthesia, vol. 47, No. 3, 2000, pp. 265-272.
Wariishi et al, "Postoperative administration of landiolol hydrochloride for patients with supraventricular arrhythmia: the efficacy of sustained intravenous infusion at a low dose" Interactive Cardiovascular and Thoracic Surgery, Oxford University Press, UK, vol. 9, No. 5, 2009, pp. 811-813.
Extended European Search Report for 13165582.1 dated Sep. 25, 2013; 10 pages.
International Preliminary Report on Patentability for PCT/EP14/58456 dated Sep. 17, 2015; 26 pages.
International Search Report and Written Opinion for PCT/EP14/58456 dated Sep. 17, 2014; 15 pages.
Written Opinion of the Int'l Preliminary Examining Authority for PCT/EP14/58456 dated Mar. 31, 2015; 9 pages.
Office Action dated Apr. 5, 2018 in corresponding Japanese Patent Appln. No. 14720107.3.
Utsumi et al. "Experiences of administration of a β1 selective blocker to patients with supraventricular tachyarrhythmia after pulmonary resection." Journal of the Japanese Association for Chest Surgery, vol. 23:3, p. 475 (2009).
Tokunaga et al. "Efficacy of the ultrashort-acting β blocker landiolol hydrochloride on patients with infant congenital heart disease complicated by supraventricular tachyarrhythmia." Journal of Pediatric Cardiology and Cardiac Surgery, vol. 25,:3, p. 432 (2009).
Suzuki et al. "Efficacy of Short-Acting β-Blockers after Cardiac Surgery." Japanese Journal of Cardiovascular Surgery, vol. 38:3, p. 175-178 (2009).
Seishima et al. "Usefulness of Short-Acting β1 Selective Blocker (Landiolol Hydrochloride) for Postoperative Tachyarrhythmia after Radical Operation of Esophageal Cancer." Japanese Journal of Gastroenterol Surgery, vol. 43:9, p. 990-995 (2010).
Sanui et al. "Low-dose landiolol for hypertension with tachycardia following neurosurgery." Journal of Anesthesia, vol. 22:195-196 (May 2008).
Nagai et al. "Urgent management of rapid heart rate in patients with atrial fibrillation/flutter and left ventricular dysfunction." Circulation Journal, Late Breaking Clinical Trial JCS (2013).
Nakano et al. "Effect of landiolol hydrochloride, an ultra-short-acting beta 1-selective blocker, on supraventricular tachycardia, atrial fibrillation and flutter after pulmonary resection." Journal of Clinical Pharmacy and Therapeutics, 37:431-435 (2012).
Takahashi et al. "Landiolol decreases a dysrhythmogenic dose of epinephrine in dogs during halothane anesthesia." Canadian Journal of Anesthesia, vol. 46:6, p. 599-604 (Jun. 1999).
Yamagishi et al., "Simulation of the Pharmacokinetics of Landiolol Hydrochloride for Tachycardiac Atrial Fibrillation in a Patient undergoing Amputation of the Lower Extremity," ICU & CCU, 2009, 33(2): 147-151.
Sakamoto, Atsuhiro, "Turning point for landiolol hydrochloride," Journal of the Japanese Society of Intensive Care Medicine, 2008, 15(4):490-491.
Seo et al. Japanese Journal of Medicine and Pharmaceutical Science, 2008, 59(1):115-118.
Kazuhiko et al., Progress in Medicine, 2007, 27(2):441-443.
Sanui, M., "Low-dose landiolol for hypertension with tachycardia following neurosurgery," Journal of Anesthesia, 2008, 22:195-196.
Seishima et al., "Usefulness of Short-Acting β1 Selective Blocker (Landiolol Hydrochloride) for Postoperative Tachyarrhythmia after Radical Operation of Esophageal Cancer," Japanese Journal of Gastroenetol. Surgery, 2010, 43(9):990-995.
Suzuki et al., "Efficacy of Short-Acting β-Blockers after Cardiac Surgery," Japanese Journal of Cardiovascular Surgery, 2009, 38(3):175-178.
Sojiro et al., Progress in Medicine, 2009, 29(12):3137-3141.
Tokunaga et al., "Efficacy of the ultrashort-acting β blocker landiolol hydrochloride on patients with infant congenital heart disease complicated by supraventricular tachyarrhythmia," Pediatric Cardiology and Cardiac Surgery, 2009, 25(3):432.
Tokunaga et al., "Management of Tachyarrhythmia with an Ultrashort-acting β-blocker; Landiolol Hydrochloride after Pediatric Cardiac Surgery," Pediatric Cardiology and Cardiac Surgery, 2009, 25(5):681-686.
Utsumi et al., "Experiences of administration of a β1 selective blocker to patients with supraventricular tachyarrhythmia after pulmonary resection," Journal of the Japanese Association for Chest Surgery, 2009, 23(3):475.
Krumpl et al., "Pharmacokinetics and -Dynamics of Low, Intermediate and High Dose Landiolol and Esmolol During Long Term Infusion in Healthy Caucasians", J Cardiovascular Pharmacol, 2018, 71(3):137-146.
Krumpl et al., "Pharmacodynamic and -kinetic Behavior of Low-, Intermediate-, and High-Dose Landiolol During Long-Term Infusion in Whites", Wolters Kluwer Health, Inc., J Cardiovascular Pharmacol, 2017, 70(1):42-51.
Sato et al., "Safety and Efficacy of Low-Dose Continuous Infusion of Landiolol, an Ultra-Short-Acting β-blocker, in Cardiac Surgery", Journal of Arrhythmia, 2011, 27:57-62.

* cited by examiner

USE OF LANDIOLOL HYDROCHLORIDE IN THE LONG-TERM TREATMENT OF TACHYARRHYTHMIAS

CROSS-REFERENCE TO RELATED APPLICATIONS

This application is the U.S. national stage of International Patent Application No. PCT/EP2014/058456, filed on Apr. 25, 2014 and entitled USE OF LANDIOLOL HYDROCHLORIDE IN THE LONG-TERM TREATMENT OF TACHYARRHYTHMIAS AND HYPERTENSION, which claims the benefit of priority under 35 U.S.C. § 119 from European Patent Application No. 13165582.1, filed Apr. 26, 2013. The disclosures of the foregoing applications are incorporated herein by reference in their entirety.

FIELD OF THE INVENTION

The invention provides a new use of landiolol hydrochloride for persistent reduction of the heart rate and/or blood pressure during the administration period compared to the heart rate and/or blood pressure before administration in the treatment of a human suffering from tachycardia or tachyarrhythmia and/or hypertension, wherein landiolol hydrochloride is administered at a constant dose of at least 5 µg/kg/min, specifically of at least 10 µg/kg/min for a period of at least 2 hours and wherein the heart rate and/or blood pressure of said patient is persistently reduced during the administration period compared to the heart rate and/or blood pressure before treatment.

BACKGROUND

Tachyarrhythmia generally refers to a heart rate that is faster than 90 beats per minute. In case of severe coronary stenosis or other severe cardiac diseases heart rates faster than 80 bpm may be considered too high (relative tachycardia).

Tachyarrhythmias may be responsible for worsening heart failure, stroke, myocardial infarction or sudden death. They may be primary or occur secondary to underlying cardiac, pulmonary or endocrine disease.

Tachyarrhythmias can be either physiologic such as sinus tachycardia occurring during exercise or pathologic as during atrial or ventricular tachycardia which can occur when irritable cells in the heart muscle or heart's electrical conduction system start to fire faster than the heart's normal rhythm. Tachyarrhythmias can start in either the upper heart chambers (atria) or lower heart chambers (ventricles). An atrial (=supraventricular) tachyarrhythmia starts in the atria and is generally classified as being atrial tachycardia (AT), atrial flutter, or tachycardic atrial fibrillation (AF). A ventricular tachyarrhythmia starts in the ventricles and is generally classified as being either a ventricular tachycardia (VT) or ventricular fibrillation (VF).

Supraventricular tachyarrhythmia is a major post-operative complication, and develops with the high frequency of 11-40% after coronary artery bypass surgery; therefore, this condition plays an important role in increased postoperative complications and duration of hospitalization (Murakami M., et al., Drug Metab. Pharmacokinet., 2005, 20(5), 337-344).

Tachycardia can be life-threatening because it can lead to ventricular fibrillation, in which the heart beats rapidly in a chaotic, purposeless fashion such that the heart cannot pump blood effectively to the body. If untreated, fibrillation can be fatal.

Long-standing tachycardia is well recognized for its potential to induce a dilated cardiomyopathy. While the exact incidence of tachycardia-mediated cardiomyopathy remains unclear, an association between tachycardia and cardiomyopathy has been recognized. Virtually every form of supraventricular tachyarrhythmia, including ectopic atrial tachycardia, nonparoxysmal junctional tachycardia, and atrial fibrillation (AF), has been associated with reversible left ventricular dysfunction or "cardiomyopathy." The development of a cardiomyopathy has also been documented with ventricular tachyarrhythmias and frequent ventricular premature beats.

Tachyarrhythmias are often treated with β-blockers which have been reported to be effective regulators of heart rate and sinus rhythm. Beta-blockers were considered useful specifically for the short and long term treatment of such diseases. These β adrenergic receptor-antagonists competitively block beta receptors, thereby inhibiting cAMP formation and preventing the events that routinely follow. $β_1$ receptor blockade causes a decrease in cardiac inotropy, chronotropy, and automaticity, culminating in a reduction of cardiac output.

There are three subgroups of beta receptors. Although these receptors may be found in more than one location in the human body, $β_1$ receptors are primarily found on cardiac myocytes, $β_2$ receptors are located chiefly in vascular and bronchial smooth muscle, $β_3$ receptors are concentrated in adipocytes, although being found in cardiac myocytes, too. During stressful conditions, endogenous catecholamine release stimulates $β_1$ receptors to promote an increase in the heart rate and contractility, whereas $β_2$ receptor stimulation induces branchiolar and arteriolar dilation. Agonists also promote insulin release glycogenolysis, and gluconeogenesis (Anderson A. C., 2008, Clin. Ped. Emergency Med., 4-16).

Blockade of $β_1$ receptors also leads to suppression of renin secretion in the kidney, thereby decreasing production of angiotensin II (a potent vasoconstrictor) and aldosterone (which promotes sodium retention). The combination of renal effects and reduced cardiac output promotes a decrease in the blood pressure. Blocking vascular smooth muscle $β_2$ receptors provides a rise in vascular tone that is clinically insignificant in most instances.

Hypertension (HTN) or high blood pressure, sometimes called arterial hypertension, is a medical condition in which the blood pressure in the arteries is elevated. Blood pressure is summarised by two measurements, systolic and diastolic, which depend on whether the heart muscle is contracting (systole) or relaxed between beats (diastole). This equals the maximum and minimum pressure, respectively. Normal blood pressure at rest is within the range of 100-140 mmHg systolic (top reading) and 60-90 mmHg diastolic (bottom reading). High blood pressure is said to be present if it is often at or above 140/90 mmHg.

Hypertension is classified as either primary (essential) hypertension or secondary hypertension; about 90-95% of cases are categorized as "primary hypertension" which means high blood pressure with no obvious underlying medical cause. The remaining 5-10% of cases (secondary hypertension) are caused by other conditions that affect the kidneys, arteries, heart or endocrine system.

Hypertension puts strain on the heart, leading to hypertensive heart disease and coronary artery disease if not treated. Hypertension is also a major risk factor for stroke, aneurysms of the arteries (e.g. aortic aneurysm), peripheral arterial disease and is a cause of chronic kidney disease. A moderately high arterial blood pressure is associated with a shortened life expectancy while mild elevation is not. Dietary and lifestyle changes can improve blood pressure control and decrease the risk of health complications, although drug treatment is still often necessary in people for whom lifestyle changes are not enough or not effective.

Esmolol hydrochloride, the first ultra short-acting adrenergic β1 adrenoreceptor blocking agent, has been widely used to aid control of tachycardia and hypertension. Esmolol is an ultra short-acting intravenous cardioselective beta-antagonist. It has an extremely short elimination half-life (mean: 9 minutes; range: 4 to 16 minutes) and a total body clearance [285 ml/min/kg (17.1 L/h/kg)] approaching 3 times cardiac output and 14 times hepatic blood flow. The alpha-distribution half-life is approximately 2 minutes. When esmolol is administered as a bolus followed by a continuous infusion, onset of activity occurs within 2 minutes, with 90% of steady-state beta-blockade occurring within 5 minutes. Full recovery from beta-blockade is observed 18 to 30 minutes after terminating the infusion. Esmolol blood concentrations are undetectable 20 to 30 minutes post infusion. The elimination of esmolol is independent of renal or hepatic function as it is metabolised by red blood cell cytosol esterases to an acid metabolite and methanol. The acid metabolite, which is renally eliminated, has 1500-fold less activity than esmolol. Clinically, esmolol was used in the past for the following: (i) situations where a brief duration of adrenergic blockade is required, such as tracheal intubation and stressful surgical stimuli; and (ii) critically ill or unstable patients in whom the dosage of esmolol is easily titrated to response and adverse effects are rapidly managed by termination of the infusion. In adults, bolus doses of 100 to 200 mg are effective in attenuating the adrenergic responses associated with tracheal intubation and surgical stimuli. For the control of supraventricular arrhythmias, acute postoperative hypertension and acute ischaemic heart disease, doses of <300 µg/kg/min, administered by continuous intravenous infusion, are used. The principal adverse effect of esmolol is hypotension (incidence of 0 to 50). The incidence of hypotension appears to increase with doses exceeding 150 µg/kg/min and in patients with low baseline blood pressure. Hypotension infrequently requires any intervention other than decreasing the dose or discontinuing the infusion. Symptoms are generally resolved within 30 minutes after discontinuing the drug. In surgical and critical care settings where clinical conditions are rapidly changing, the pharmacokinetic profile of esmolol allows the drug to provide rapid pharmacological control and minimises the potential for serious adverse effects.

Miwa Y. et al. (2010, Circulation Journal, 74, 856-863) describe the effect of landiolol in the treatment of electrical refractory storm.

Takahashi S. et al. (2000, Can. J. Anesth., 47, 265-272) describe studies on the effect of landiolol on hemodynamic response to acute theophylline intoxication inducing tachyarrhythmia in animals.

Morisaki A. et al. (2012, Gen. Thorac. Cardiovasc. Surg., 60, 386-390) describes continuous very-low-dose of 2 µg/kg/min-5 µg/kg/min of landiolol for about 10 days in treating postoperative atrial tachycardia in patients with poor left ventricular function.

Wariishi S. et al. (2009, Interactive Cardiovasc. Thoracic Surgery, 9, 811-813) describes the low dose administration of landiolol hydrochloride in patients with postoperative supraventricular arrhythmia.

Studies on different doses of landiolol hydrochloride infused for eleven minutes during anesthesia in patients of different age and sex are disclosed by Mizuno J. et al. (2007, Eur. J. Clin. Pharmacol., 63, 243-252).

Kubo K. et al. (2005, J. Anesth., 19, 174-176) describe the use of landiolol at a dose of 40 ug/kg/min during cesarean section in a patient with Romano-Ward syndrome. Administration was stopped 10 minutes before end of surgery.

Nagai R. et al. (2013, Circulation J., 77, 908-916) disclose the use of landiolol to control tachycardia in patients with left ventricular dysfunction. The dosage is adjusted to the range of 1-10 µg/kg/min.

It was shown that long-term administration of beta-blockers can be associated with an increase in myocardial β-adrenergic receptor density (Hellbrunn S. et al., Circulation, 1989, 79, 483-490, Nanoff C. et al., 1990, Basic Res. Cardiol., 85, 88-95). The β-adrenergic receptor increase may not only lead to the restoration of β-adrenergic sensitivity in cases of heart failure treatment but, in cases of tachycardia, it may also lead to a beta-blocker tolerance which thus needs increased dosages and shorter administration intervals.

It has been reported that sudden discontinuation of the administration of similar compounds (propranolol hydrochloride) from patients who suffered from angina or other coronary heart diseases worsened the condition or led to cardiac infarction (Harrison D C and Alderman E L, 1976, Chest, 69(1), 1-2; Hausen T., 1981, MMW Münch Med Wochenschr., 123(42), 1583-4). In data sheets for Ono Act (landiolol hydrochloride, Ono Pharmaceuticals. Revised edition November 2012) and esmolol hydrochloride (Brevibloc, Aug. 10, 2009) it is noted that careful observation is required when discontinuing the administration of landiolol or that an overshoot after termination of esmolol administration cannot be ruled out.

Additionally, sensitization of receptor mediated response may lead to withdrawal syndromes after termination of beta-blocker administration (Peters J. R. et al., 1985, 107, 43-52).

Furthermore, long term treatment with intravenously administered beta-blockers can lead to negative side effects such as infusion site reactions including inflammation and induration, like edema, erythema, skin discoloration, burning at the infusion site, thrombophlebitis, and local skin necrosis from extravasation phlebitis, which side effects are commonly minimized by administering the diluted formulation.

There is still an unmet demand for providing a long-term treatment of tachyarrhythmia or tachycardia that avoids negative side effects but are effective in the treatment without the need of increasing the dosage due to tolerance effects thereby promoting vascular irritation and overshoot reactions.

BRIEF DESCRIPTION OF THE INVENTION

The object of the invention is solved by the present invention.

The invention provides a formulation of landiolol hydrochloride in a therapeutically efficient amount for use in the treatment of a subject suffering from tachycardia, tachyarrhythmia and/or hypertension, wherein landiolol hydrochloride is administered at a constant dose of about 5 µg/kg/min, specifically more than (>) 5 µg/kg/min, preferably at least 10 µg/kg/min for a period of at least 2 hours, preferably for at least 4 hours, preferably for at least 6 hours, preferably for at least 12 hours, preferably for at least 20 hours, preferably for at least 24 hours, preferably for at least 2 days, preferably for more than two days and wherein the heart rate and/or blood pressure of said patient are persistently reduced during the administration period compared to the heart rate and/or blood pressure before treatment, specifically as opposed to other short acting beta blocker such as esmolol.

According to a further embodiment of the invention, the constant dose of landiolol hydrochloride is at least 15 µg/kg/min, specifically at least 20 µg/kg/min, specifically at least 25 µg/kg/min, specifically at least 30 µg/kg/min, specifically at least 35 µg/kg/min, specifically at least 40 µg/kg/min.

According to a further embodiment of the invention the heart rate and/or blood pressure are reduced at least 5%, preferably between 10% and 50% compared to the heart rate and/or blood pressure before treatment with landiolol.

Overshoot is not occurring after termination of administration and normal heart rate and/or blood pressure are attained within a few minutes, specifically within 5 to 20 minutes and more specifically, said normal heart rate and/or blood pressure are preserved for at least 30 minutes, preferably for at least 60 minutes, more preferred at least 120 minutes after termination of administration of landiolol-hydrochloride as opposed to esmolol where an overshoot occurs within minutes and may be maintained hours thus leading to increased heart rate and/or blood pressure.

According to the invention, the formulation thus shows a reduced or no overshoot effect with regard to the heart rate and/or blood pressure after termination of administration.

According to an embodiment of the invention, landiolol-hydrochloride is at a concentration of about 1 to 30 mg/mL, preferably about 5 to 15 mg/mL.

According to the embodiment of the invention, the administration of a pharmaceutical composition comprising landiolol-hydrochloride for the use according of the present invention, may be done in a variety of ways, including orally, subcutaneously, intravenously, intraarterially, intracoronary, intranasally, intraotically, transdermally, mucosally, topically, e.g., gels, salves, lotions, creams, etc., intraperitoneally, intramuscularly, intrapulmonary, e.g. employing inhalable technology or pulmonary delivery systems, vaginally, parenterally, rectally, or intraocularly.

A specific embodiment provides a formulation wherein landiolol hydrochloride is a lyophilized powder reconstituted to obtain a ready to use i.v. solution, optionally the i.v. solution has a pH of up to 6.5 and as a further option, said i.v. solution is administered as continuous infusion.

According to an embodiment, said i.v. solution is administered as maintenance infusion at a dose of between 5 to 100 µg/kg/min, preferably 10 to 100 µg/kg/min, preferably between 10 to 50 µg/kg/min.

In an embodiment, the i.v. solution is local tissue tolerant at the infusion site, preventing local venous irritation or skin necrosis at the infusion site.

In a specific embodiment, the subject is suffering from supraventricular tachycardia.

In a further specific embodiment, the subject is suffering from hypertension, specifically from primary or secondary hypertension or hypertensive crisis.

The inventive use is specifically for treating a subject, wherein said subject is
  a. suffering from tachycardia selected from, supraventricular tachycardia, ventricular tachycardia, hypertension and non-compensatory sinus tachycardia, atrial tachycardic fibrillation, atrial flutter in perioperative, postoperative, or other circumstances where persistent control of the ventricular rate is desirable, or
  b. in need of blood pressure lowering perioperatively or in other acute situations or during aortic dissection or for controlled hypotension to avoid blood loss in ear, nose, or throat surgery or for diagnostic purposes.

Specifically, said subject is having cardiac decompensation and/or hyperhydratation and/or renal decompensation and/or hypernatremia and/or hyperchloramic acidosis and/or hyperhydratation.

According to a further embodiment, the formulation or preparation is used for a subject receiving a positive inotropic drug, specifically selected from the group of Berberine, Calcium, Calcium sensitisers like Levosimendan, cardiac myosin activators like Omecamt iv, Catecholamines selected from the group of Dopamine, Dobutamine, Dopexamine, Epinephrine (adrenaline), Isoprenaline (isoproterenol), Norepinephrine (noradrenaline), ephedrine, Digoxin, Digitalis; eicosanoids like Prostaglandins; phosphodiesterase inhibitors selected from the group of Enoximone, Milrinone, Amrinone, Theophylline; Glucagon or Insulin or a sympathomimetic drug, specifically selected from the group of β agonists.

According to a specific embodiment, the subject that can be treated using the formulation of the invention is suffering from intoxication from positive inotropic drug or sympathomimetic drug.

Additionally, also a method of producing a ready-to-use solution of landiolol hydrochloride for the inventive use is provided by reconstituting a lyophilized powder consisting of pure landiolol hydrochloride with a solvent, wherein said solvent is optionally devoid of alcohol, in an amount necessary to obtain a ready-to-use solution at a concentration of about 5 to 15 mg/mL.

As a further embodiment, a formulation is provided where landiolol is present in an already diluted ready to use preparation.

DETAILED DESCRIPTION OF THE INVENTION

It could surprisingly be shown that landiolol-hydrochloride, being an ultra short-effective beta-blocker, can be used for long term administration without showing any tolerance effects thus leading to a persistent reduction of heart rate and avoiding any overshoot effect upon termination of the administration.

This effect could not be shown by another ultra short-effective beta blocker, esmolol. Long term administration of esmolol leads to a relative increase of the heart rate and blood pressure already after 60 minutes of administration demonstrating the absence of any overt beta blocking effect and additionally, after termination of administration, the heart rate and blood pressure raise immediately over control values.

Long term administration of landiolol-hydrochloride can also achieve heart rate values and/or blood pressure values which are significantly lower than the heart rate and/or blood pressure values achieved under esmolol long-term treatment. Thus, the invention provides a new use of landiolol hydrochloride as a parenteral formulation in the treatment of a subject suffering from tachycardia, tachyarrhythmia and/or hypertension, wherein landiolol-hydrochloride is administered for a period of at least 2 hrs, specifically for a period of at least 2.5 hrs, specifically for a period of at least 3 hrs, specifically at least 4 hrs, specifically for a period of at least 5 hrs, specifically at least 6 hrs, specifically at least 8 hrs, specifically at least 10 hrs, specifically at least 12 hrs, specifically at least 14 hrs, specifically at least 16 hrs, specifically at least 18 hrs, specifically at least 20 hrs, specifically at least 24 hrs, specifically at least 2 days, specifically for more than two days and wherein the heart rate of said patient is persistently reduced during the administration period compared to the heart rate before landiolol hydrochloride treatment.

Landiolol (CAS 133242-30-5), administered as landiolol hydrochloride (CAS 144481-98-1), chemical name (−)-[(S)-2,2-dimethyl-1,3-dioxolan-4-yl]methyl 3-[4-[(S)-2-hydroxy-3-(2-morpholinocarbonylamino)ethylamino]propoxy]phenylpropionate monohydrochloride, empirical formula $C_{25}H_{39}N_3O_8HCl$ (molecular weight 546.05) is an ultra-short acting β1-selective blocker.

The term "heart rate" means the heart beats per minute.

The term "blood pressure" means systolic and diastolic blood pressure expressed in mmHg or kPa.

The term "constant" with regard to the administration of landiolol-hydrochloride means that the dose is not changed during the respective time period, thus there is no steady increase or decrease of dosage during said time interval.

Thus the patient can be administered a high dose landiolol-hydrochloride for long term treatment without the side effects of tolerance or overshoot reaction. The term "normal" heart rate is related to a heart rate while the subject is relaxed but awake, in a neutrally temperate environment, and not having recently exerted himself or herself nor having been subject to stress. The typical normal (resting) heart rate in adults is 60-80 beats per minute (bpm), heart rates between 50 and 60 are also considered normal under resting conditions or during sedation.

The terms "tachycardia" and "tachyarrhythmia" as used herein are understood in the broadest sense, including all disease conditions associated with fast or irregular heart rate, in particular a condition in which the heart contracts at a rate greater than 90-100/min in adults. In some cases, specifically in case of severe coronary stenosis or other severe cardiac diseases, heart rates above 80 bpm may be considered too high (relative tachycardia).

Herein tachycardia specifically refers to pathologic tachycardia accompanying anoxia, such as that caused by anaemia; congestive heart failure; haemorrhage; or shock. Tachycardia acts to increase the amount of oxygen delivered to the cells of the body by increasing the rate at which blood circulates through the vessels.

Herein, the term "supraventricular tachycardia" (SVT) defines a condition presenting as a rapid heart rhythm originating at or above the atrioventricular node. Although SVT can be due to any supraventricular cause, the term is most often used to refer to a specific example, paroxysmal supraventricular tachycardia (PSVT), two common types being atrioventricular reciprocating tachycardia and AV nodal reentrant tachycardia.

In general, SVT is caused by one of two mechanisms: The first is re-entry; the second is automaticity. Re-entry (such as AV nodal reentrant tachycardia and atrioventricular reciprocating tachycardia) often presents with an almost immediate onset with sudden increase in heart rate. A person experiencing this type of PSVT may feel the heart rate accelerate from 60 to 200 beats per minute or more. Typically, when it reverts to normal rhythm, this is also sudden.

The main pumping chamber, the ventricle, is protected (to a certain extent) against excessively high rates arising from the supraventricular areas by a 'gating mechanism' at the atrioventricular node, which allows only a proportion of the fast impulses to pass through to the ventricles. In a condition called Wolff-Parkinson-White Syndrome, a 'bypass tract' avoids this node and its protection and the fast rate may be directly transmitted to the ventricles. This situation has characteristic findings on ECG.

In automatic types of SVT (atrial tachycardia, junctional ectopic tachycardia), there is more typically a gradual increase and decrease in the heart rate. These are due to an area in the heart that generates its own electrical signal.

Supraventricular tachycardias can be contrasted with the potentially more dangerous ventricular tachycardias rapid rhythms that originate within the ventricular tissue.

The term "hypertension" or, as equivalent "high blood pressure" or "arterial hypertension", is a medical condition in which the blood pressure in the arteries is elevated. Blood pressure is summarised by two measurements, systolic and diastolic, which depend on whether the heart muscle is contracting (systole) or relaxed between beats (diastole). This equals the maximum and minimum pressure, respectively. Normal blood pressure at rest is within the range of 100-140 mmHg systolic (top reading) and 60-90 mmHg diastolic (bottom reading). High blood pressure is said to be present if it is at or above 140/90 mmHg. Severely elevated blood pressure, i.e. equal to or greater than a systolic 180 or diastolic of 110, sometimes termed malignant or accelerated hypertension, is referred to as a "hypertensive crisis", as blood pressure at this level confers a high risk of complications.

Herein the terms "subject" refers to human beings in need of such treatment.

According to a further embodiment, it surprisingly turned out that the typical side effects of local venous skin irritations or inflammatory reactions at the site of injection induced by esmolol could be avoided by long-term administration of landiolol-hydrochloride using the formulation according to the invention, specifically long term treatment did not bring about any blushing, erythema, pain, inflammation, induration, phlebitis and thrombosis.

"Long-term administration" means an administration which takes at least 30 minutes.

"High dose" means a dose of landiolol of more than 20 μg/kg/min, specifically more than 25 μg/kg/min, more than 30 μg/kg/min, more than 35 μg/kg/min, more preferably more than 40 μg/kg/min.

Persistent reduction means that the heart rate and/or blood pressure are constantly lower than the heart rate and/or blood pressure immediately before start of the landiolol hydrochloride administration. Persistent reduction of the heart rate and/or blood pressure may be due to the lack of developing a tolerance syndrome by the subject. Thereby, the sensitivity of the subject towards the administration of the beta blocker is not significantly increased which further has the advantage that termination of the administration of the beta blocker does not result in hypersensitivity towards β adrenergic agonists being administered or are circulating in the subject's blood stream.

According a specific embodiment of the invention, landiolol hydrochloride can be combined with any β adrenergic agonist treatment, for example it can be combined with positive inotropic substances like dobutamine or amrinone or with any other known $β_1$ and $β_2$ stimulating agents.

According to a specific embodiment, the heart rate and/or blood pressure are reduced at least 1%, preferably at least 2%, preferably at least 3%, preferably at least 4%, preferably at least 5%, preferably between 10% and 50% compared to the heart rate before treatment.

"Rebound effect" is the emergence or re-emergence of symptoms that were either absent or controlled while taking a medication, but appear when the same medication is discontinued or reduced in dosage. In the case of re-emergence, the severity of the symptoms is often worse than pretreatment levels.

An overshoot effect can occur after termination of the medication with a severe raise of heart rate as opposed to the achievement of a normal heart rate. Severe raise means that the heart rate and blood pressure is 2.5%, specifically 5%, specifically 10%, specifically more than 10%, more specifically more than 25% higher compared to the heart rate before treatment. Alternatively, the increase of the heart rate can be indicated by an increase of 10 to 30 bpm and/or an increase of the blood pressure by 5-30 mmHg. An overshoot effect can specifically occur when the administration of the active compound is immediately terminated without stepwise reduction of the administration dosage.

"Tolerance" occurs when providing long term treatment, specifically when administrating beta blocker one usually must consider the possibility of occurrence of habituation towards the drug which makes it necessary to increase the dosage and/or interval of administering said medicament or to change the active agent used for the treatment of the specific symptom or disease. Tolerance necessitates an increase in dosage to achieve the same drug effect.

Thus, according to an embodiment of the invention, tolerance and overshoot effects are avoided or significantly reduced after long term administration of landiolol-hydrochloride and normal heart rate and/or blood pressure are achieved within a few minutes, specifically within 5 to 20 minutes after termination of the administration of landiolol-hydrochloride and said effect being continuing for at least 15 minutes, specifically at least 30 minutes, specifically at least 60 minutes, more specifically at least 120 minutes after the administration of landiolol-hydrochloride.

Specifically, no significant overshoot effect occurs after termination of administration of landiolol-hydrochloride.

In contrast, esmolol shows a significant tolerance and overshoot effect thus leading to significantly increased heart rate and blood pressure that are above normal pre dose values.

According to the invention any composition comprising landiolol hydrochloride as active agent may be used which is available at present and applicable for application.

Said landiolol HCl compositions may contain different concentrations of landiolol, for example, but not limited to 10 mg, 12.5 mg, 20 mg, 50 mg, 300 mg or 600 mg.

The formulation of the invention can be present in any form which can be used for administration, in particular as pharmaceutical preparation.

Administration of a pharmaceutical composition comprising landiolol-hydrochloride for the use according to the present invention may be done in a variety of ways. It may be administered parenterally, orally, optically, vaginally, mucosally, nasally, rectally, topically, e.g., gels, salves, lotions, creams, etc., or buccally.

The term "parenteral" as used herein refers to subcutaneous, intracutaneous, intravenous, intramuscular, intraarticular, intrarterial, intrasynovial, intrasternal, intrathecal, intralesional, intraperitoneal, intratracheal, intracranial, intracoronar, intrapulmonary, e.g. employing inhalable technology or pulmonary delivery systems.

Exemplary formulations as used for parenteral administration include those suitable for subcutaneous, intramuscular or intravenous injection as, for example, a sterile solution, emulsion or suspension.

For example, the formulation of the invention can be administered as liquid or powder. It can be administered topically, intravenously, subcutaneously, by inhalation, e.g. to administer an aerosol, or by using a nebulizer, or in orally available form like tablets or capsules.

Aerosolized delivery of the landiolol hydrochloride may result in a more homogeneous distribution of the agent in a lung, so that deep lung delivery is obtained.

The formulation can be administered with any pharmaceutically acceptable substances or carriers or excipients as known in the art. These can be for example, but are not restricted to water, neutralizing agents like NaOH, KOH, stabilizers, DMSO, saline, betaine, taurine etc.

Any stabilizers, preservatives, buffers, tonicity agents or excipients may further be comprised in the parenteral formulations. Specifically, stabilising agents may be, but are not limited to polyethylene glycol, cyclodextrin, ethanol. Buffer agents may be, but are not limited to, sodium hydroxide, glacial acetic acid, hydrochloric acid, sodium acetate dehydrate, potassium chloride, potassium dihydrogen phosphate, disodium hydrogen phosphate anhydride. As an example, the tonicity agent may be sodium chloride and as example of an excipient, mannitol may be used.

The term "pharmaceutically acceptable" means approved by a regulatory agency of the Federal or a state government or listed in the U.S.

The term "carrier" refers to a diluent, adjuvant, excipient, or vehicle with which the pharmaceutical composition is administered. Saline solutions and aqueous dextrose and glycerol solutions can also be employed as liquid carriers, particularly for injectable solutions. Suitable excipients include starch, glucose, lactose, sucrose, gelatine, malt, rice, flour, chalk, silica gel, sodium stearate, glycerol monostearate, talc, sodium chloride, dried skim milk, glycerol, propylene, glycol, water, ethanol and the like. Examples of suitable pharmaceutical carriers are described in "Remington's Pharmaceutical Sciences" by E. W. Martin. The formulation should be selected according to the mode of administration.

Landiolol-hydrochloride may further be provided as a lyophilized powder which is reconstituted to obtain a ready to use i.v. solution or as aqueous solution. Alternatively, the solutions may be diluted and prepared from stock solutions by adjusting the respective concentration of landiolol-hydrochloride. As a further alternative, landiolol may be already provided in a diluted ready to use preparation.

Said formulations may be, for example, available under the trade names Rapibloc®, Onoact® or Corebeta®.

According to one embodiment, the landiolol hydrochloride formulation comprises landiolol HCl and D-mannitol.

The pH of the formulation may be between 6 and 7, specifically about 6.5.

According to an embodiment of the invention, landiolol-hydrochloride is at a concentration of about 1 to 30 mg/mL, specifically about 10 to 20 mg/mL, specifically about 5 to 15 mg/mL.

The formulation may be administered parenterally, more specifically intravenously. For long term treatment, continuous infusion is the preferred administration form, the solution may specifically administered as maintenance infusion at a dose of between 0.1 to 100 µg/kg/min, specifically between 5 to 50 µg/kg/min, more specifically between 10 to 50 µg/kg/min.

Whereby the formulation due to its excellent local tolerability can be administered using peripheral veins.

The administration of landiolol hydrochloride after at least two hours at constant dose can be terminated immediately or the dose can also be stepwise reduced, either within a short period of several minutes or hours As an alternative, the dose of landiolol hydrochloride can also be increased after the minimum period of two hours, i.e. it may be increased up to 40 µg/kg/min or even more than 40 µg/kg/min, depending on the need of the patient and the condition. Said increase of dosage can be gradually or stepwise.

The present invention specifically provides the use of landiolol-hydrochloride for long term treatment of subjects suffering from tachycardia selected from supraventricular tachycardia, ventricular tachycardia or hypertension and non-compensatory sinus tachycardia, atrial fibrillation, atrial flutter in perioperative, postoperative, or other circumstances where persistent control of the ventricular rate is desirable, or subjects who are in need of blood pressure lowering, for example perioperatively or in other acute situations or during aortic dissection, or for controlled hypotension to avoid blood loss in ear, nose, or throat surgery or for diagnostic purposes.

The invention also provides a method of treating subjects suffering from tachycardia selected from supraventricular tachycardia, ventricular tachycardia and non-compensatory sinus tachycardia, atrial fibrillation, atrial flutter in perioperative, postoperative, or other circumstances where persistent control of the ventricular rate is desirable, or subjects in need of blood pressure lowering, for example perioperatively or in other acute situations or during aortic dissection, or for controlled hypotension to avoid blood loss in ear, nose, or throat surgery or for diagnostic purposes.

Landiolol hydrochloride long term treatment may also be used for subjects having cardiac decompensation, hyperhydratation, renal decompensation, hypernatremia, hyperchloramic acidosis and/or hyperhydratation.

The administration of positive inotropic drugs may lead to severe side effects like the development of tachycardia (see for example Alhashemi J. A. et al., Brit. J. Anaesthes., 2005, 95(5), 648-650).

According to a further embodiment, the formulation is used for a subject receiving a positive inotropic drug or is suffering from intoxication due to the administration of an inotropic drug, specifically selected from the group of Berberine, Calcium, calcium sensitisers like Levosimendan, cardiac myosin activators like Omecamtiv, catecholamines selected from the group of Dopamine, Dobutamine, Dopexamine, Epinephrine (adrenaline), Isoprenaline (isoproterenol), Norepinephrine (noradrenaline), ephedrine, Digoxin, Digitalis; Eicosanoids like Prostaglandins; phosphodiesterase inhibitors selected from the group of Enoximone Milrinone, Amrinone, Theophylline; Glucagon or Insulin or a sympathomimetic drug, specifically selected from the group of $\beta_1$ and or $\beta_2$ agonists.

The invention provides the use of landiolol hydrochloride for persistent reduction of the heart rate and/or blood pressure during the administration period of landiolol hydrochloride for producing a medicament for the treatment of a human suffering from tachycardia, tachyarrhythmia and/or hypertension, wherein landiolol hydrochloride is administered at a constant dose of at least 5 µg/kg/min, specifically of >5 µg/kg/min for a period of at least 2 hours.

The invention also provides a method of treating a patient with tachycardia or tachyarrhythmia, specifically with supraventricular tachycardia, and/or hypertension, wherein said patient is administered a constant dose of more than 5 µg/kg/min, specifically at least 10 µg/kg/min landiolol hydrochloride for a period of at least 1.5 hours, specifically of at least 2 hours and wherein the heart rate of said patient is thereby persistently reduced during the administration period compared to the patient's heart rate before treatment.

According to a specific embodiment of the invention, a treatment regimen is provided wherein the subject is administered a) 5 µg/kg/min landiolol hydrochloride for two hours, b) 10 µg/kg/min are administered for two hours and c) 40 µg/kg/min is administered for at least two hours.

The invention furthermore comprises the following items:
1. Formulation of landiolol hydrochloride for persistent reduction of the heart rate and/or blood pressure during the administration period of landiolol hydrochloride in the treatment of a human suffering from tachycardia, tachyarrhythmia and/or hypertension, wherein landiolol hydrochloride is administered at a constant dose of at least 5 µg/kg/min for a period of at least 1.5 hours, preferably for a period of at least 2 hours.
2. The formulation for use according to item 1, wherein the constant dose of landiolol hydrochloride is more than 5 µg/kg/min, specifically at least 10 µg/kg/min, specifically at least 15 µg/kg/min, specifically at least 20 µg/kg/min, specifically at least 25 µg/kg/min, specifically at least 30 µg/kg/min, specifically at least 35 µg/kg/min, specifically at least 40 µg/kg/min.
3. The formulation for use according to items 1 or 2, wherein landiolol hydrochloride is administered for at least 3 hours, preferably for at least 4 hours, preferably for at least 6 hours, preferably for at least 12 hours, preferably for at least 24 hours, preferably for at least 2 days, preferably for more than two days.
4. The formulation for use according to items 1 to 3, wherein the heart rate is reduced at least 5%, preferably between 10% and 50% compared to the heart rate before treatment.
5. The formulation for use according to items 1 to 4, wherein no overshoot effect occurs after termination of administration of landiolol hydrochloride.
6. The formulation for use according to items 1 to 5, wherein a normal heart rate is reached within 5 to 20 minutes after termination of administration.
7. The formulation for use according to items 1 to 6, wherein said landiolol hydrochloride is at a concentration of about 1 to 30 mg/mL, preferably about 5 to 15 mg/mL.
8. The formulation for use according to items 1 to 7, wherein said landiolol hydrochloride is a lyophilized powder reconstituted to obtain a ready to use solution or a formulation wherein landiolol is provided in a diluted ready to use preparation.
9. The formulation for use according to items 1 to 8, wherein said solution has a pH of up to 6.5.
10. The formulation for use according to items 1 to 9, wherein said solution is administered as oral, subcutaneous, intravenous, intraarterial, intracoronary, intranasal, transdermal, topical, interpulmonary administration, specifically said solution is administered as continuous intravenous infusion, optionally using peripheral veins.
11. The formulation for use according to items 1 to 10, wherein said solution is administered as maintenance infusion at a dose of between 15 to 100 µg/kg/min, preferably between 10 to 50 µg/kg/min.
12. The formulation for use according to items 1 to 11, wherein said solution is local tissue tolerant at the infusion site, preventing local venous irritation or skin necrosis at the infusion site.
13. The formulation for use according to items 1 to 12 in the treatment of supraventricular tachycardia.
14. The formulation for use according to items 1 to 12 in the treatment of hypertension.

15. The formulation for use according to any one of items 1 to 14, wherein said subject is
    a) suffering from tachycardia selected from, supraventricular tachycardia, ventricular tachycardia, non-compensatory sinus tachycardia, atrial fibrillation, atrial flutter and/or hypertension in perioperative, postoperative, or other circumstances where persistent control of the ventricular rate is desirable, or
    b) in need of blood pressure lowering or for diagnostic purposes.
16. The formulation for use according to items 1 to 15, wherein said subject is having cardiac decompensation, hyperhydratation, renal decompensation, hypernatremia, hyperchloramic acidosis and/or hyperhydratation.
17. The formulation according to items 1 to 16, wherein said subject receiving a positive inotropic drug, specifically selected from the group of dobutamine, amrinone or a sympathomimetic drug, specifically selected from the group of beta 1, beta 2 agonists. phophodiesterease inhibitors or Calcium sensitizers.
18. Formulation according to items 1 to 17, wherein said subject is suffering from intoxication from positive intotropic and/or chronotropic drug or sympathomimetic drug.

The examples described herein are illustrative of the present invention and are not intended to be limitations thereon. Different embodiments of the present invention have been described according to the present invention. Many modifications and variations may be made to the techniques described and illustrated herein without departing from the spirit and scope of the invention. Accordingly, it should be understood that the examples are illustrative only and are not limiting upon the scope of the invention.

EXAMPLES

Example 1

A single centre prospective, randomized, double blind, crossover, pharmacokinetic, safety and tolerability study to compare long-term infusion administration of AOP LDLL600 against esmolol in healthy volunteers was performed.

Landiolol hydrochloride lyophilized (LDLL600) comprises 600 mg landiolol hydrochloride, 600 mg mannitol, pH 6.5. The primary packing of LDLL600 is 50 ml vial, the reconstitution volume is 50 ml and the final product concentration is 12 mg/mL landiolol HCl.

Study:

12 subjects were administered AOP LDLL600 or Esmolol (Brevibloc, 2500 mg/250 ml) in 1:1 ratio in double-blind, randomized, cross-over setting. PK, systemic cardiovascular and local tolerability and safety of the 24 h-long term infusions of three dose levels of both IMPs during each treatment period were assessed.

|  | Landiolol | Esmolol | Duration |
|---|---|---|---|
| Low, µg/kg/min | 10 | 50 | 2 h |
| Medium, µg/kg/min | 20 | 100 | 2 h |
| High, µg/kg/min | 40 | 200 | 20 h |

Landiolol was infused over 24 h in a dose of 10 µg/KG/min (2 hrs), followed by 20 µg/KG/min (2 hrs), followed by 40 µg/KG/min for 20 hrs.

Dosing algorithm was body weight divided by 20, 10 and 5 in ml/h giving 10, 20 and 40 µg/KG/min at a concentration of 12 mg/ml. No severe adverse drug reactions, mild local reactions, 1 severe local reaction (Esmolol High Dose).

Local tolerability of Landiolol compared to Esmolol is clearly better:

Local reactions Landiolol: 2/12 (16.7%)

Esmolol: 7/14 (50.0%)

TABLE 1

| Dose | | Landiolol | Esmolol | p< |
|---|---|---|---|---|
| | | (beats per minute) | | |
| Control | | 67.8 | 67 | |
| | Time (min) | | | |
| low | 12 | 62.7 | 65.2 | 0.258 |
| | 16 | 60.3 | 65.4 | 0.016 |
| | 30 | 59.5 | 62.6 | 0.205 |
| | 60 | 57.8 | 63.6 | 0.035 |
| | 120 | 56.2 | 63.8 | 0.004 |
| medium | 240 | 56.1 | 63.7 | 0.033 |
| high | 720 | 57.5 | 67.9 | 0.001 |
| | 1200 | 53.6 | 67.9 | 0.001 |
| end | 1440 | | | |
| | Time after administration (min): | | | |
| | 12 | 63.5 | 74.7 | 0.003 |
| | 16 | 67 | 74 | 0.033 |
| | 30 | 70 | 76.8 | 0.033 |
| | 60 | 69.2 | 73.1 | 0.096 |
| | 120 | 66.8 | 70.2 | 0.233 |

Example 2

A single centre prospective, randomized, double blind, crossover, pharmacokinetic, safety and tolerability study to compare long-term infusion administration of AOP LDLL600 against esmolol in healthy volunteers was performed.

Landiolol hydrochloride lyophilized (LDLL600) comprises 600 mg landiolol hydrochloride, 600 mg mannitol, pH 6.5. The primary packing of LDLL600 is 50 ml vial, the reconstitution volume is 50 ml and the final product concentration is 12 mg/mL landiolol HCl.

Study:

12 subjects were administered AOP LDLL600 or Esmolol (Brevibloc, 2500 mg/250 ml) in 1:1 ratio in double-blind, randomized, cross-over setting. PK, systemic cardiovascular and local tolerability and safety of the 24 h-long term infusions of three dose levels of both IMPs during each treatment period were assessed.

|  | Landiolol | Esmolol | Duration |
|---|---|---|---|
| Low, µg/kg/min | 10 | 50 | 2 h |
| Medium, µg/kg/min | 20 | 100 | 2 h |
| High, µg/kg/min | 40 | 200 | 20 h |

Landiolol was infused over 24 h in a dose of 10, 20 and 40 µg/KG/min, i.e. 10 µg/KG/min landiolol were administered for 2 hrs, followed by 2 hrs administration of 20 µg/KG/min and further followed by 20 hrs administration of 40 µg/KG/min.

Post-infusion follow up measurements were performed immediately after 20 hrs administration study, i.e. 2, 4 min etc. after stop of landiolol administration.

Dosing algorithm was body weight divided by 20, 10 and 5 in ml/h giving 10, 20 and 40 μg/KG/min at a concentration of 12 mg/ml. No severe adverse drug reactions, mild local reactions, 1 severe local reaction (Esmolol High Dose).

Tolerance state (esmolol, MD, HD): the results of table 2 show that even the dosage×100% (>high dose) does not provide any additive effect.

L=LDLL600
E=Esmolol
LD=low dose, MD=medium dose, HD=high dose; FU=post-infusion follow up

TABLE 2

|  | Time point | Mean (SD) (beats per minute) | Mean (SD) | p-value* |
|---|---|---|---|---|
| Landiolol $L^{LD}$ | Predose | 67.3 (8.18) | | |
| | 2 min | 65.6 (5.09) | −1.8 (7.77) | 0.718 |
| | 3 min | 64.8 (6.82) | −2.5 (7.48) | 0.484 |
| | 4 min | 64.6 (6.97) | −2.8 (6.38) | 0.196 |
| | 6 min | 65.7 (8.78) | −1.7 (7.97) | 0.461 |
| | 8 min | 63.8 (6.57) | −3.6 (9.07) | 0.392 |
| | 12 min | 62.7 (7.71) | −4.7 (10.99) | 0.213 |
| | 16 min | 60.3 (6.72) | −7.1 (5.32) | 0.003 |
| | 20 min | 60.0 (6.05) | −7.3 (10.51) | 0.031 |
| | 30 min | 59.5 (8.55) | −7.8 (12.55) | 0.071 |
| | 60 min | 57.8 (8.05) | −9.6 (11.89) | 0.010 |
| | 90 min | 58.1 (7.14) | −9.3 (11.33) | 0.006 |
| | 2 h | 56.2 (5.89) | −11.2 (11.75) | 0.004 |
| $L^{MD}$ | Predose | 56.2 (5.89) | −11.2 (11.75) | 0.004 |
| | 2 min | 56.3 (6.48) | −11.1 (10.73) | <.001 |
| | 3 min | 57.6 (5.02) | −9.8 (7.90) | 0.003 |
| | 4 min | 56.4 (6.87) | −10.9 (9.26) | <.001 |
| | 6 min | 56.2 (7.86) | −11.2 (11.10) | 0.002 |
| | 8 min | 57.7 (7.24) | −9.7 (10.96) | 0.001 |
| | 12 min | 54.5 (6.07) | −12.8 (10.17) | <.001 |
| | 16 min | 56.9 (6.88) | −10.4 (11.42) | 0.002 |
| | 20 min | 54.5 (6.86) | −12.8 (10.52) | 0.001 |
| | 30 min | 58.3 (8.53) | −9.0 (11.92) | 0.014 |
| | 60 min | 56.0 (5.17) | −11.3 (9.86) | 0.001 |
| | 90 min | 57.2 (6.79) | −10.2 (10.81) | <.001 |
| | 2 h | 56.1 (7.38) | −11.3 (9.41) | <.001 |
| $L^{HD}$ | Predose | 56.1 (7.38) | −11.3 (9.41) | <.001 |
| | 2 min | 57.8 (5.43) | −9.6 (8.69) | 0.002 |
| | 3 min | 57.4 (6.40) | −9.9 (9.92) | 0.004 |
| | 4 min | 54.8 (5.45) | −12.6 (9.52) | <.001 |
| | 6 min | 57.7 (7.38) | −9.7 (11.01) | 0.010 |
| | 8 min | 56.7 (6.62) | −10.7 (10.76) | <.001 |
| | 12 min | 57.9 (8.13) | −9.4 (12.21) | 0.022 |
| | 16 min | 56.0 (6.80) | −11.3 (10.71) | 0.002 |
| | 20 min | 55.9 (6.35) | −11.4 (9.74) | <.001 |
| | 30 min | 56.8 (7.23) | −10.5 (10.30) | <.001 |
| | 60 min | 61.9 (8.93) | −5.4 (13.14) | 0.226 |
| | 90 min | 62.5 (5.95) | −4.8 (11.24) | 0.146 |
| | 2 h | 64.3 (5.25) | −3.0 (9.59) | 0.516 |
| | 4 h | 60.4 (5.25) | −6.9 (11.24) | 0.049 |
| | 8 h | 57.5 (5.96) | −9.8 (10.39) | 0.002 |
| | 12 h | 56.5 (6.08) | −10.8 (10.17) | <.001 |
| | 16 h | 53.6 (4.89) | −13.8 (10.01) | <.001 |
| | 20 h (end) | 61.7 (5.87) | −5.7 (11.51) | 0.087 |
| | Landiolol Infusion stop | | | |
| $L^{FU}$ | Predose | 61.7 (5.87) | −5.7 (11.51) | 0.087 |
| | 20 h 2 min | 60.6 (5.50) | −6.8 (11.98) | 0.105 |
| | 20 h 4 min | 60.8 (4.04) | −6.5 (9.88) | 0.054 |
| | 20 h 6 min | 61.4 (5.43) | −5.9 (9.79) | 0.083 |
| | 20 h 8 min | 61.7 (5.33) | −5.7 (10.63) | 0.104 |
| | 20 h 12 min | 63.5 (6.11) | −3.8 (10.00) | 0.334 |
| | 20 h 16 min | 67.0 (8.92) | −0.3 (14.69) | 0.556 |
| | 20 h 20 min | 67.0 (8.29) | −0.3 (11.89) | 0.834 |
| | 20 h 30 min | 70.0 (5.70) | 2.7 (9.47) | 0.301 |
| | 21 h | 69.2 (9.64) | 1.8 (12.70) | 0.609 |
| | 22 h | 66.8 (8.43) | −0.5 (9.97) | 0.634 |
| | 24 h | 71.5 (4.96) | 4.2 (10.34) | 0.169 |
| | 26 h | 72.6 (5.26) | 5.3 (9.97) | 0.085 |
| Esmolol | | | | |
| $E^{LD}$ | Predose | 67.6 (7.87) | | |
| | 2 min | 66.9 (6.28) | −0.7 (6.22) | 0.540 |
| | 3 min | 65.7 (4.91) | −1.9 (5.34) | 0.171 |
| | 4 min | 65.6 (6.44) | −2.1 (7.64) | 0.278 |
| | 6 min | 66.0 (4.52) | −1.6 (5.96) | 0.380 |
| | 8 min | 65.5 (4.35) | −2.1 (7.05) | 0.368 |

TABLE 2-continued

|  | Time point | Mean (SD)<br>(beats per minute) | Mean (SD) | p-value* | |
|---|---|---|---|---|---|
|  | 12 min | 65.2 (4.74) | −2.4 (6.77) | 0.198 | |
|  | 16 min | 65.4 (5.51) | −2.3 (7.58) | 0.434 | |
|  | 20 min | 65.6 (7.07) | −2.0 (9.49) | 0.402 | |
|  | 30 min | 62.6 (5.05) | −5.1 (6.29) | 0.011 | |
|  | 60 min | 63.6 (4.67) | −4.1 (8.00) | 0.123 | |
|  | 90 min | 64.1 (4.99) | −3.5 (6.55) | 0.075 | |
|  | 2 h | 63.8 (4.89) | −3.9 (7.12) | 0.050 | |
| $E^{MD}$ | Predose | 63.8 (4.89) | −3.9 (7.12) | 0.050 | |
|  | 2 min | 63.4 (7.88) | −4.3 (10.36) | 0.063 | |
|  | 3 min | 62.6 (5.50) | −5.1 (8.40) | 0.047 | |
|  | 4 min | 64.9 (9.04) | −2.7 (8.96) | 0.155 | |
|  | 6 min | 63.9 (5.10) | −3.8 (7.45) | 0.114 | |
|  | 8 min | 62.1 (4.46) | −5.6 (7.54) | 0.007 | |
|  | 12 min | 61.8 (5.07) |  | 0.016 | |
|  | 16 min | 64.1 (5.02) | −3.5 (7.14) | 0.093 | |
|  | 20 min | 62.6 (4.33) | −5.0 (7.34) | 0.024 | |
|  | 30 min | 62.1 (5.00) | −5.6 (8.20) | 0.017 | |
|  | 60 min | 66.2 (5.04) | −1.4 (10.41) | 0.722 | Tolerance state |
|  | 90 min | 65.4 (6.17) | −2.2 (8.59) | 0.669 | Tolerance state |
|  | 2 h | 63.7 (4.86) | −3.9 (7.75) | 0.091 | Tolerance state |
| $E^{HD}$ | Predose | 63.7 (4.86) | −3.9 (7.75) | 0.091 | Tolerance state |
|  | 2 min | 65.1 (7.10) | −2.5 (8.96) | 0.330 | Tolerance state |
|  | 3 min | 64.4 (4.38) | −3.2 (8.99) | 0.248 | Tolerance state |
|  | 4 min | 64.5 (4.74) | −3.1 (8.16) | 0.221 | Tolerance state |
|  | 6 min | 64.9 (4.29) | −2.8 (8.97) | 0.434 | Tolerance state |
|  | 8 min | 63.9 (7.14) | −3.7 (10.45) | 0.186 | Tolerance state |
|  | 12 min | 64.8 (4.39) | −2.9 (9.19) | 0.400 | Tolerance state |
|  | 16 min | 64.4 (7.16) | −3.3 (8.32) | 0.274 | Tolerance state |
|  | 20 min | 67.3 (7.26) | −0.4 (11.69) | 0.941 | Tolerance state |
|  | 30 min | 65.4 (5.69) | −2.3 (9.26) | 0.467 | Tolerance state |
|  | 60 min | 72.6 (6.64) | 4.9 (9.60) | 0.064 | Tolerance state |
|  | 90 min | 73.6 (4.57) | 5.9 (8.95) | 0.025 | Tolerance state |
|  | 2 h | 73.9 (4.55) | 6.2 (9.32) | 0.040 | Tolerance state |
|  | 4 h | 70.4 (5.03) | 2.8 (9.60) | 0.246 | Tolerance state |
|  | 8 h | 67.9 (5.95) | 0.3 (10.34) | 0.577 | Tolerance state |
|  | 12 h | 68.4 (8.30) | 0.7 (10.94) | 0.436 | Tolerance state |
|  | 16 h | 67.9 (7.49) | 0.3 (9.27) | 0.724 | Tolerance state |
|  | 20 h (end) | 69.1 (6.40) | 1.5 (9.05) | 0.421 | Tolerance state |
|  | Esmolol Infusion stop | | | | |
| $E^{FU}$ | Predose | 69.1 (6.40) | 1.5 (9.05) | 0.421 | |
|  | 20 h 2 min | 69.0 (4.88) | 1.4 (7.57) | 0.516 | |
|  | 20 h 4 min | 71.3 (7.04) | 3.6 (8.77) | 0.151 | |
|  | 20 h 6 min | 73.1 (7.89) | 5.4 (8.11) | 0.025 | overshoot |
|  | 20 h 8 min | 73.1 (7.57) | 5.4 (8.10) | 0.028 | overshoot |
|  | 20 h 12 min | 74.7 (8.62) | 7.1 (8.43) | 0.004 | overshoot |
|  | 20 h 16 min | 74.0 (7.99) | 6.4 (7.44) | 0.009 | overshoot |
|  | 20 h 20 min | 74.4 (7.04) | 6.8 (7.17) | 0.005 | overshoot |
|  | 20 h 30 min | 76.8 (8.51) | 9.1 (8.04) | <.001 | overshoot |
|  | 21 h | 73.1 (7.50) | 5.5 (8.15) | 0.032 | overshoot |
|  | 22 h | 70.2 (7.06) | 2.6 (8.02) | 0.208 | |
|  | 24 h | 72.1 (7.37) | 4.5 (9.51) | 0.090 | |
|  | 26 h | 72.8 (9.74) | 5.1 (10.85) | 0.097 | |

*Wilcoxon signed-rank test of difference from zero for changes from the last measurement before the start of the first IMP administration in treatment period

The invention claimed is:

1. A method of reducing the heart rate of a subject suffering from supraventricular tachycardia, wherein the method consists of the step of administering landiolol hydrochloride parenterally to the subject at a constant dose of more than 20 μg/kg/min for a period of from 2 to 20 hours, wherein the dose is not higher than 40 μg/kg/min.

2. The method of claim 1, wherein the constant dose of landiolol hydrochloride is at least 25 μg/kg/min, at least 30 μg/kg/min, or at least 35 μg/kg/min.

3. The method of claim 1, wherein landiolol hydrochloride is administered for at least 4 hours, for at least 6 hours, or for at least 12 hours.

4. The method of claim 1, wherein the heart rate of the subject is reduced by at least 5%, or by between 10% and 50%, compared to the heart rate of the subject before the administration of landiolol hydrochloride.

5. The method of claim 1, wherein no overshoot effect occurs after termination of the administration of landiolol hydrochloride to the subject.

6. The method of claim 1, wherein the subject's heart reaches a normal rate within 5 to 20 minutes after termination of administration of landiolol hydrochloride to the subject.

7. The method of claim 1, wherein said landiolol hydrochloride is at a concentration of about 1 mg/mL to 30 mg/mL, or at a concentration of about 5 to 15 mg/mL.

8. The method of claim 1, wherein said landiolol hydrochloride is provided as a solution.

9. The method of claim 8, wherein said solution has a pH of up to 6.5.

10. The method of claim 8, wherein said solution is administered by a route selected from the group consisting of subcutaneous administration, intravenous administration, intraarterial administration, and intracoronary administration.

11. The method of claim 8, wherein said solution is local tissue tolerant at the infusion site, thereby preventing local venous irritation or skin necrosis at the infusion site.

12. The method of claim 1, wherein said subject is suffering from intoxication due to a positive intotropic drug or a sympathomimetic drug.

13. The method of claim 8, wherein the solution is prepared by reconstituting a lyophilized powder comprising landiolol hydrochloride.

14. The method of claim 10, wherein the solution of landiolol hydrochloride is administered as a continuous intravenous infusion.

15. The method of claim 1, wherein said landiolol hydrochloride is provided for a period of up to 4 hours.

* * * * *